(12) United States Patent
Iskarous et al.

(10) Patent No.: US 9,108,199 B2
(45) Date of Patent: Aug. 18, 2015

(54) AUTOMATIC TEST TUBE RECAPPER

(75) Inventors: Reda R. Iskarous, Wood River, IL (US);
James I. Wonders, Wood River, IL (US)

(73) Assignee: LPG. Consulting, Inc., Wood River, FL (US)

( * ) Notice: Subject to any disclaimer, the term of this patent is extended or adjusted under 35 U.S.C. 154(b) by 630 days.

(21) Appl. No.: 13/486,743

(22) Filed: Jun. 1, 2012

(65) Prior Publication Data
US 2013/0318915 A1   Dec. 5, 2013

(51) Int. Cl.
*B67B 3/064*   (2006.01)
*B01L 3/00*   (2006.01)
*B65B 7/28*   (2006.01)
*G01N 35/04*   (2006.01)

(52) U.S. Cl.
CPC .............. *B01L 3/50825* (2013.01); *B67B 3/064* (2013.01); *G01N 35/04* (2013.01); *B01L 2200/025* (2013.01); *B01L 2300/046* (2013.01); *B65B 7/2807* (2013.01); *B65B 7/2821* (2013.01); *B67B 3/0645* (2013.01); *G01N 2035/0405* (2013.01); *G01N 2035/0465* (2013.01)

(58) Field of Classification Search
IPC ...................... B65B 7/2807,7/2821; B67B 1/00, B67B 1/04, 3/064, 3/0645, 3/06
See application file for complete search history.

(56) References Cited

U.S. PATENT DOCUMENTS

| | | | | |
|---|---|---|---|---|
| 2,596,408 | A * | 5/1952 | Johnson et al. | 53/72 |
| 4,081,069 | A * | 3/1978 | Ono | 198/381 |
| 4,987,726 | A * | 1/1991 | Petho et al. | 53/510 |
| 4,995,781 | A * | 2/1991 | Herzog | 414/680 |
| 5,050,722 | A * | 9/1991 | Beswick | 198/392 |
| 5,493,849 | A * | 2/1996 | Itoh | 53/489 |
| 5,669,209 | A * | 9/1997 | Dewees et al. | 53/490 |
| 5,890,349 | A * | 4/1999 | Heisler et al. | 53/485 |
| 7,322,458 | B1 * | 1/2008 | McDonald et al. | 198/389 |
| 7,401,446 | B2 * | 7/2008 | Perazzo et al. | 53/317 |
| 7,770,358 | B2 * | 8/2010 | Sink et al. | 53/367 |
| 7,992,365 | B2 * | 8/2011 | Uebel et al. | 53/490 |
| 8,276,741 | B1 * | 10/2012 | Zittel | 198/382 |
| 2003/0041565 | A1 * | 3/2003 | Banks et al. | 53/415 |
| 2009/0151305 | A1 * | 6/2009 | Cassoni et al. | 53/485 |
| 2009/0166153 | A1 * | 7/2009 | Dotson et al. | 198/393 |
| 2010/0307109 | A1 * | 12/2010 | Pedrazzini | 53/317 |

* cited by examiner

*Primary Examiner* — Christopher Harmon
(74) *Attorney, Agent, or Firm* — Don W. Weber

(57) ABSTRACT

An automatic test tube recapper is presented that is capable of recapping thousands of test tubes per day. Specially designed caps are poured into an upper triangular shaped hopper. The randomly oriented caps are transported by a pair of belts to an upper slide. Misaligned caps are rejected and fall back into the hopper, while properly aligned caps slide down the slide to a cap catch, one at a time. A hammer shaft then drives the cap into the top of the test tube until the cap is firmly seated. The hammer shaft reverses, which withdraws the shaft upwards. As the hammer shaft moves upwards, it triggers a pair of arms that allows another cap to fall into the cap catch. A conveyor also automatically moves the next uncapped test tube under the cap. The cycle then repeats itself.

8 Claims, 22 Drawing Sheets

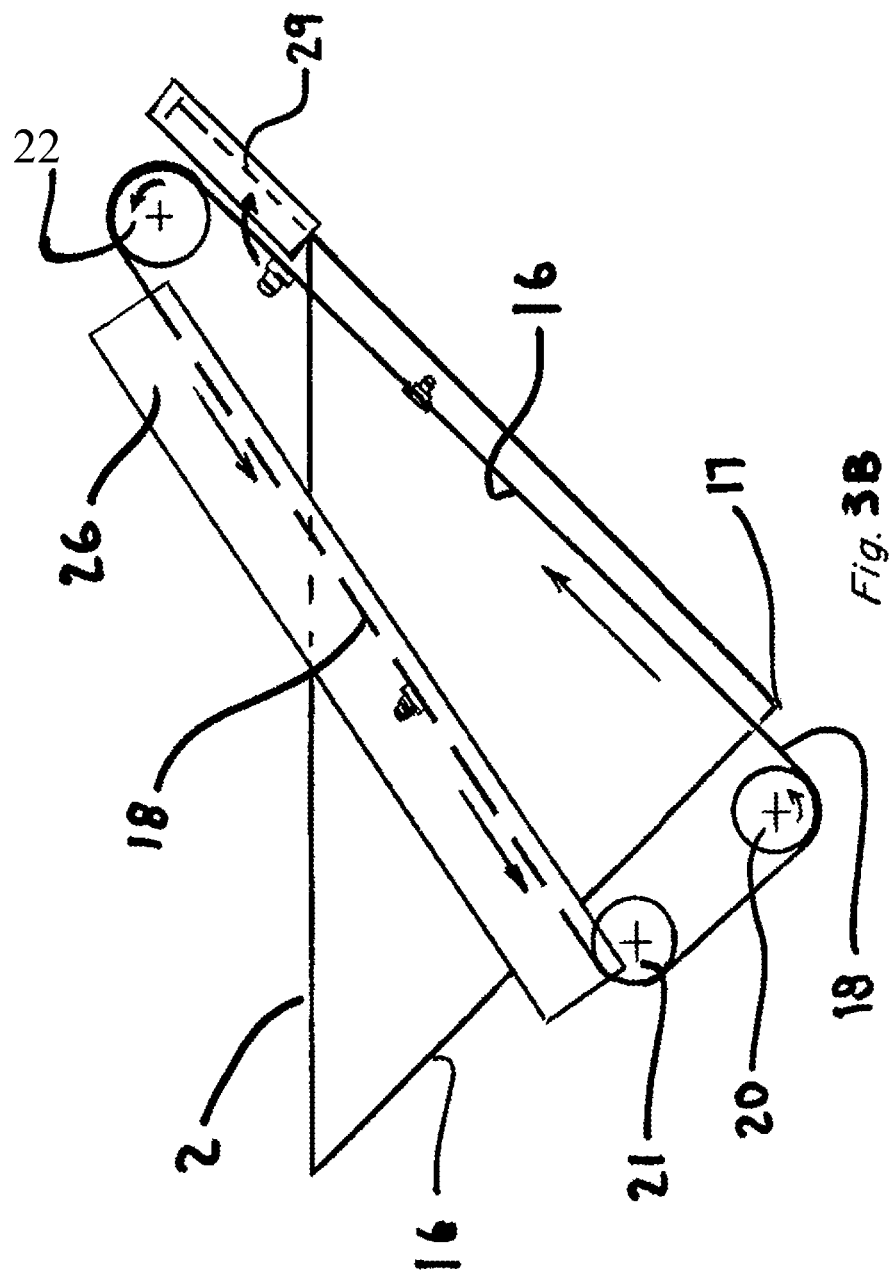

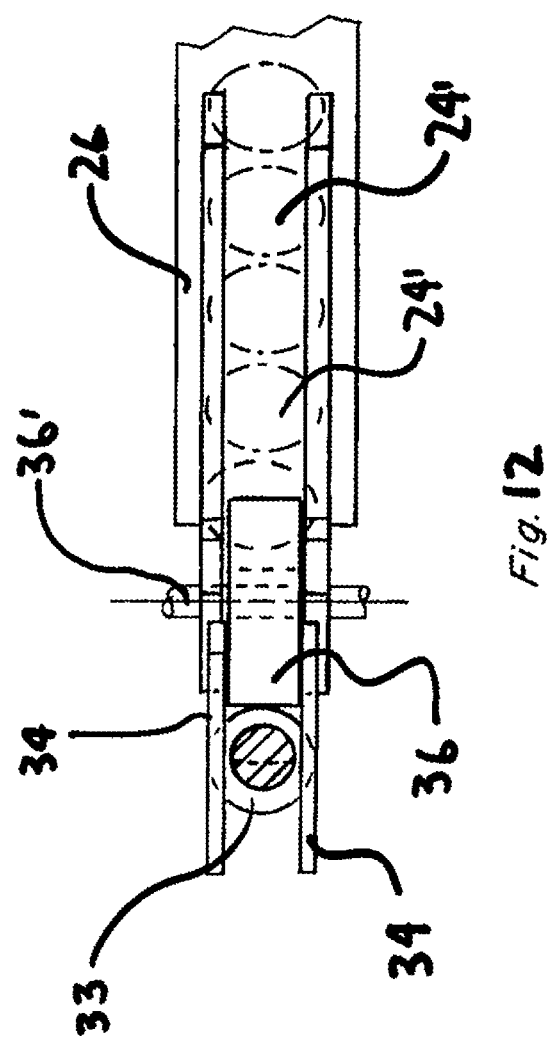

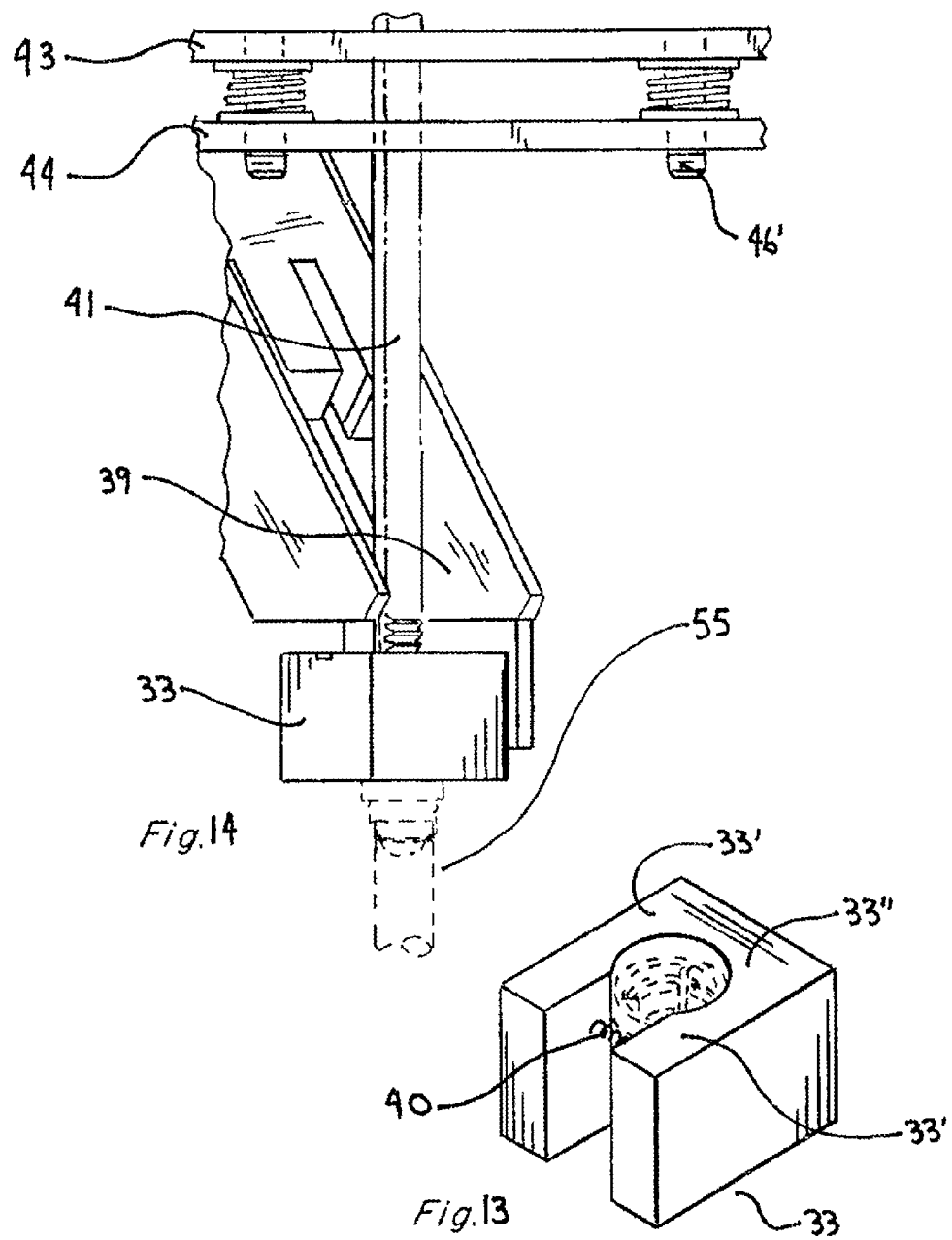

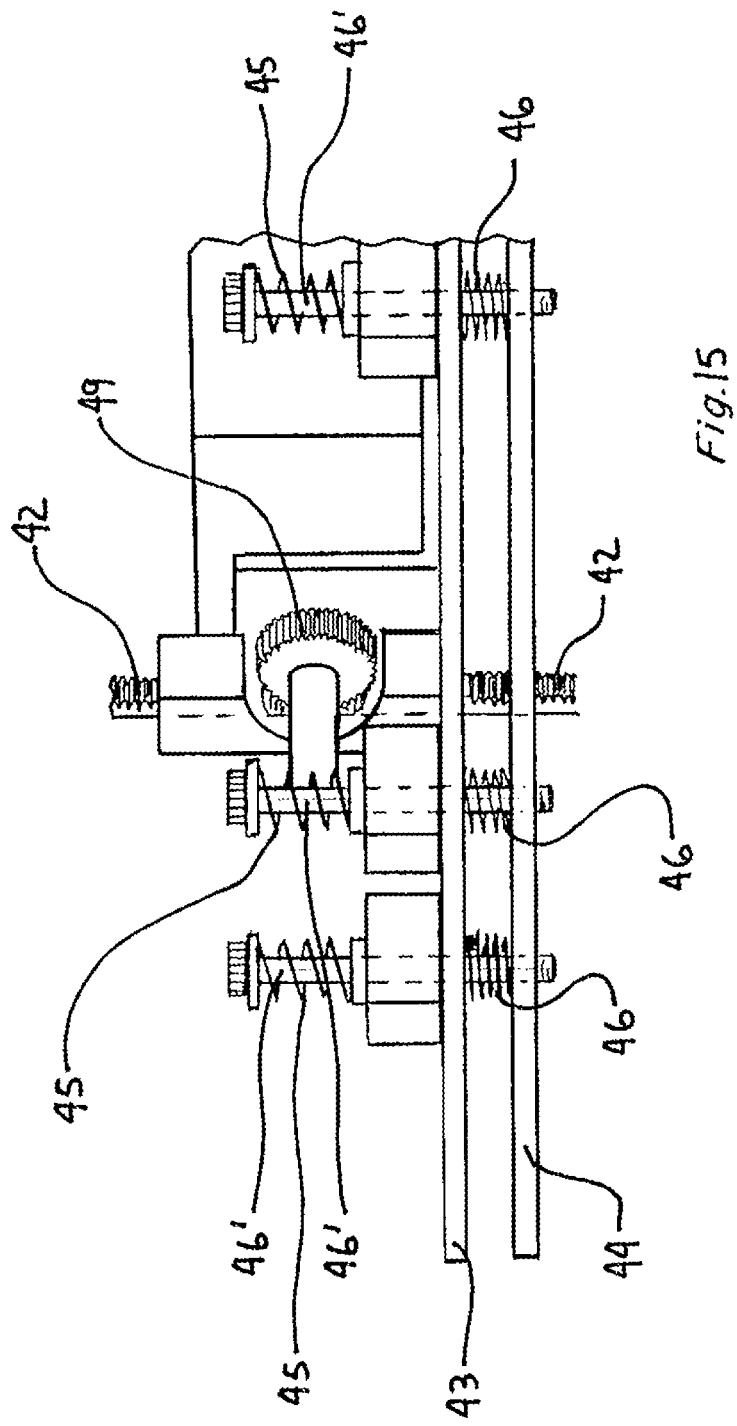

AUTOMATIC TEST TUBE RECAPPER

BACKGROUND OF THE INVENTION

Figure 1:
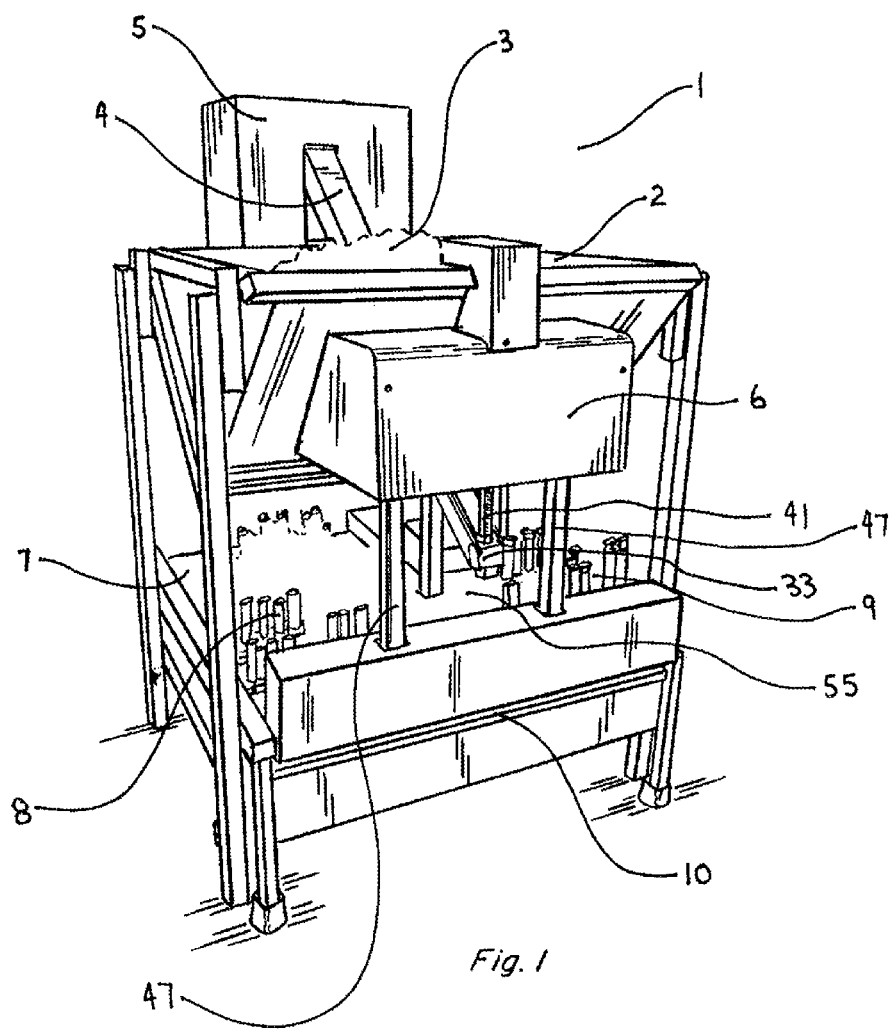

This invention relates to the field of medical and forensic science testing equipment. More particularly, an automatic test tube recapper for recapping test tubes after the contents of the test tubes has been used is presented.

In the medical and forensic science fields test tubes are normally used to contain blood, saliva, swab and other specimens taken from the human body. These test tubes are generally cylindrical in shape with an open top. Test tubes usually have several standard diameters, namely approximately 13 mm or 16 mm. They can also come in standard heights, namely approximately 75 mm or 100 mm. The test tube is usually capped with an original rubber or plastic stopper at the top to prevent contamination of the specimen and to protect the sample and keep it inside the test tube.

Test tubes are used in large quantities, particularly in the medical and pharmaceutical industries and in forensic laboratories. Larger labs or hospitals may test as many as 10,000 specimens per day, using 10,000 test tubes and caps. Once the tests have been accomplished, it is necessary to recap the specimen test tubes for proper storage. It is an object of this invention to provide a machine that automatically recaps test tubes once the tests have been done.

Since test tubes come in different diameters, it would be useful and economical to have a single cap capable of capping several different diameter tubes. It is another object of this invention to provide a single test tube cap that is able to receive several standard size diameter test tubes.

Since standard test tubes used in the laboratory come in different heights, it would be convenient and economical to provide a machine that is capable of recapping different height test tubes. It is a still further object of this invention to provide an automatic test tube recapper that is capable of recapping test tubes of different heights and diameters.

Other and further objects of this invention will become obvious upon reading the below described specification.

BRIEF DESCRIPTION OF THE INVENTION

A fully automatic test tube recapper capable of recapping thousands of test tubes per day of various sized test tubes has an upper hopper with a triangular cross-section for receiving specially designed test tubes caps. The caps are poured into the hopper and are contained within the hopper in random orientations. A pair of spaced apart silicon transport belts is separated by the diameter of the caps. These continuous belts transport the caps upwards towards a slide. Properly aligned caps are then transferred to the slide. The slide slopes downwardly toward a capping station. Misaligned caps are ejected from the transport belt before they reach the slide and are fed back into the hopper.

Caps are lined up and stopped at the bottom of the slide by a cap incrementing disc that allows one cap per cycle to drop onto a cap catch station. Directly above the cap catch station is a hammer drive. Directly below the cap catch station is the uncapped test tube.

As the hammer cycle begins, the hammer shaft is driven downwardly into the top of the cap. The cap then releases from its cap catch and is inserted into the top of the test tube. The hammer drive is located on a movable, spring-loaded base that has a movement sensor. When the cap is firmly inserted into the test tube, the hammer base rises. The reversed direction of the hammer base signals the device to withdraw the hammer shaft from the cap. As the hammer shaft rises, the incrementing disc releases another single cap into the cap catch as the conveyor for the test tube rack moves the test tube rack and a new uncapped test tube under the cap catch station. The cycle then repeats itself.

The caps are adapted to receive different diameter tubes. Since the hammer shaft stops and reverses only once the caps have been firmly inserted into the test tubes, the device is capable of recapping different height test tubes.

BRIEF DESCRIPTION OF THE DRAWING FIGURES

Figure 2:
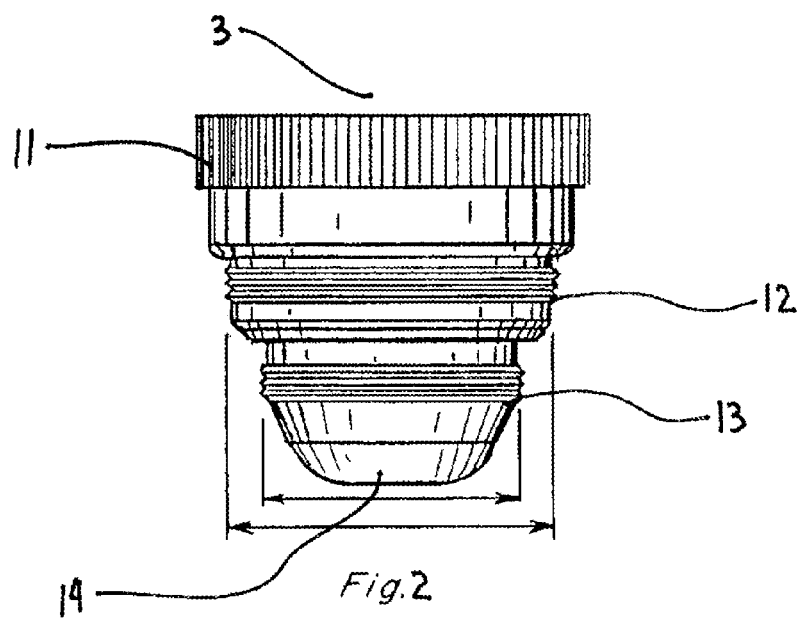
Figure 2A:
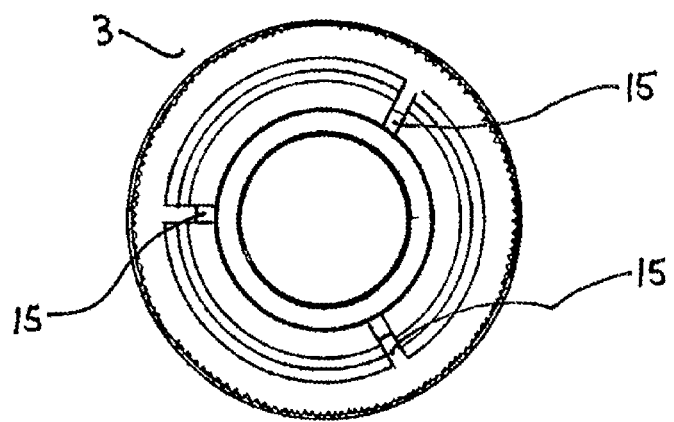
Figure 2B:
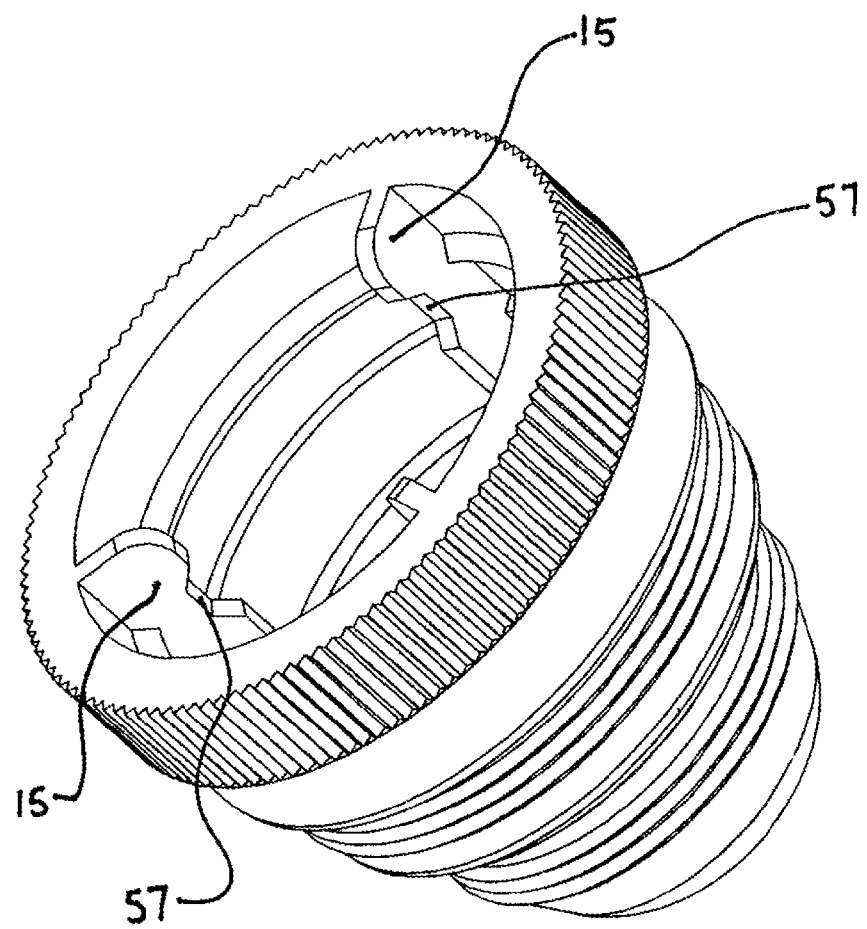
Figure 3A:
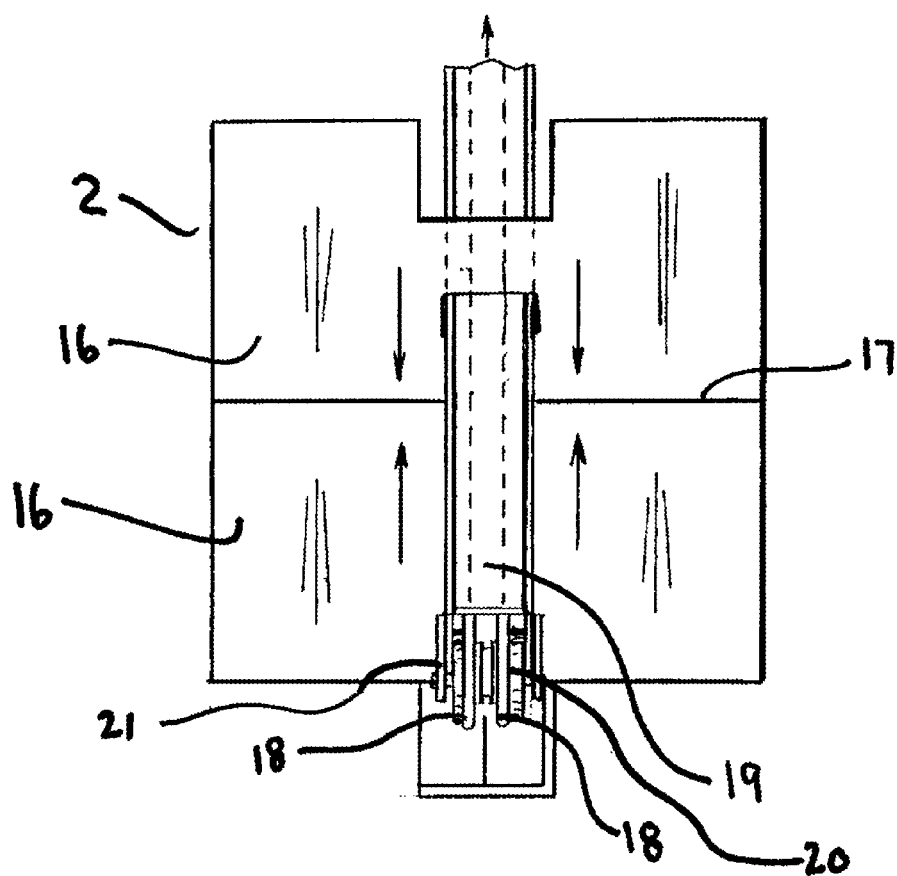
Figure 4:
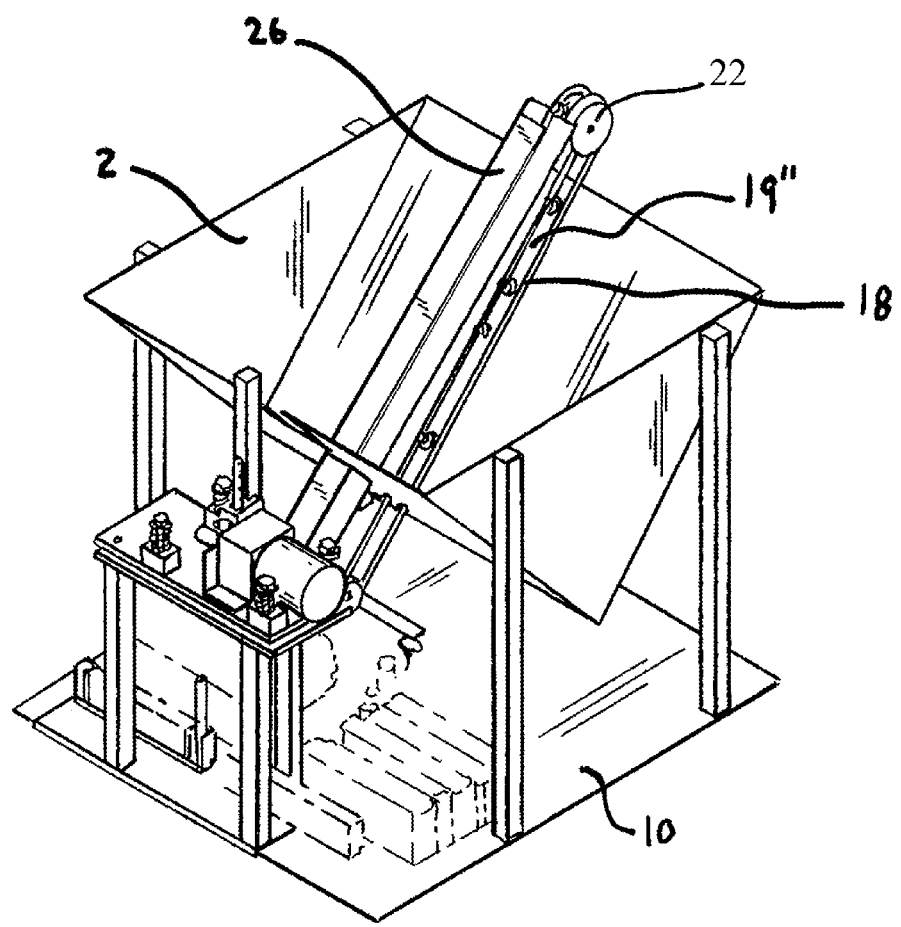
Figure 5:
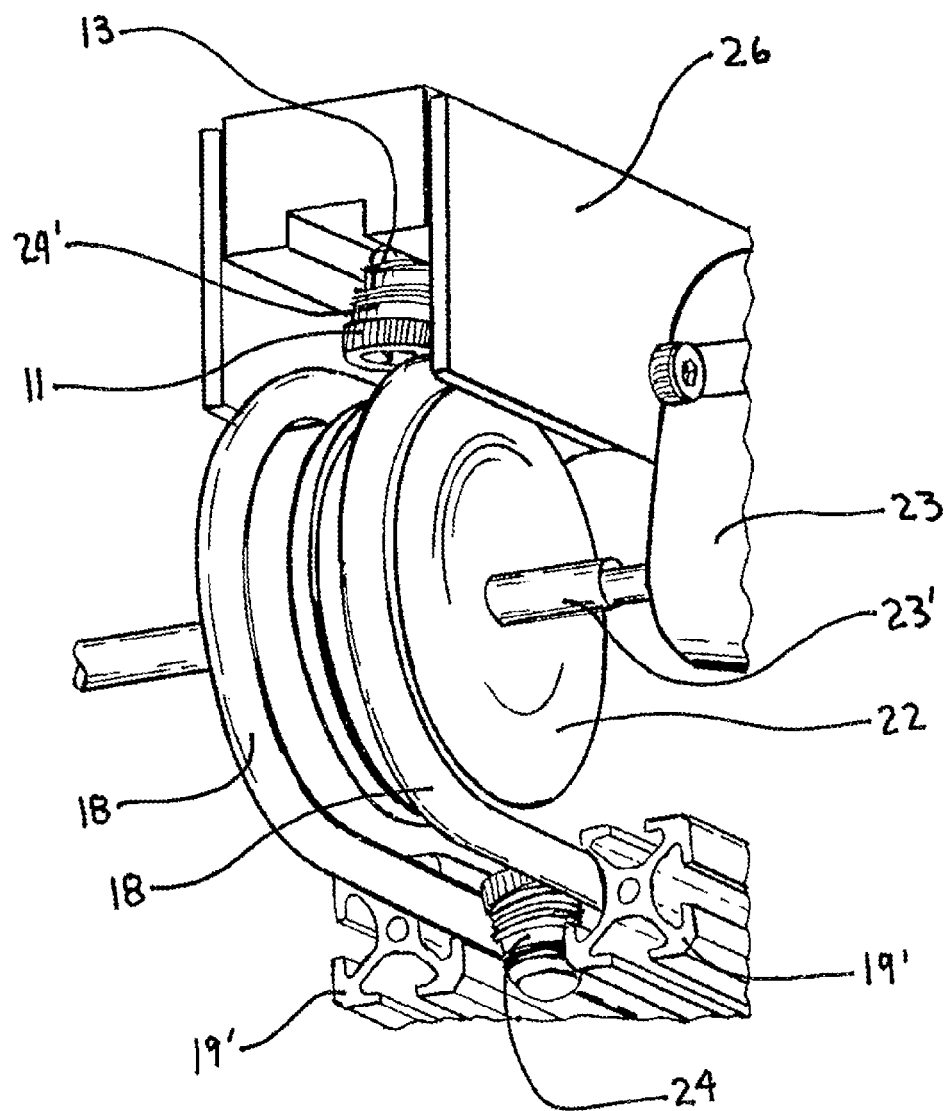
Figure 6:
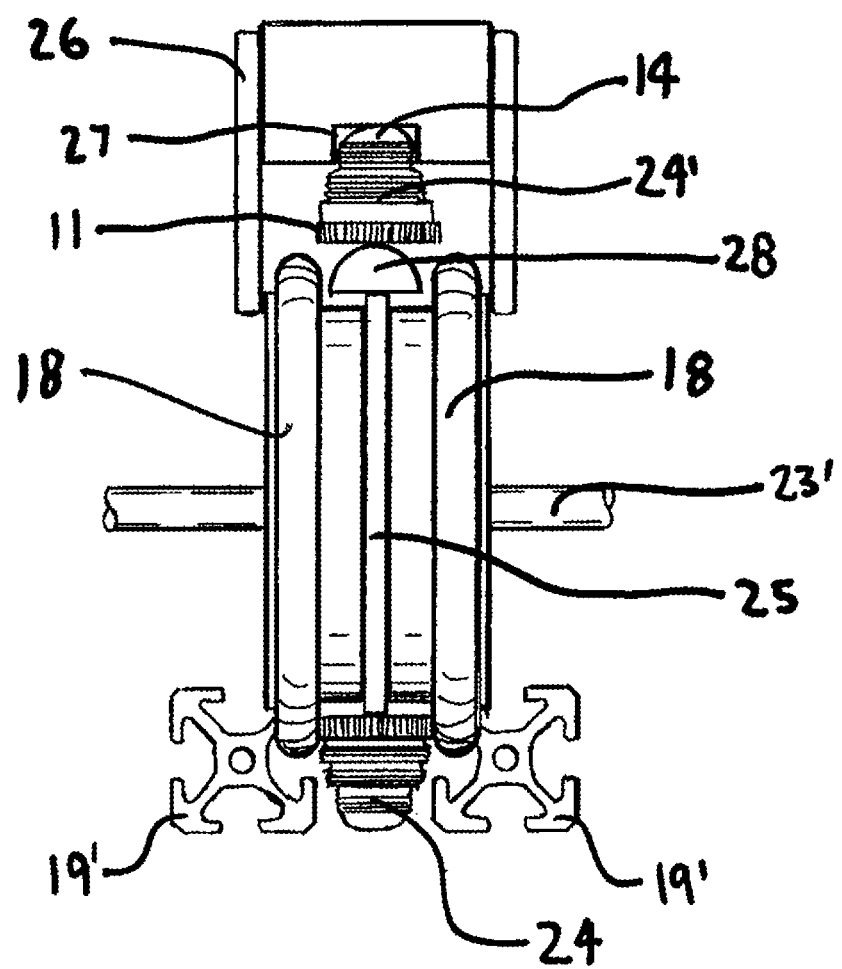
Figure 7B:
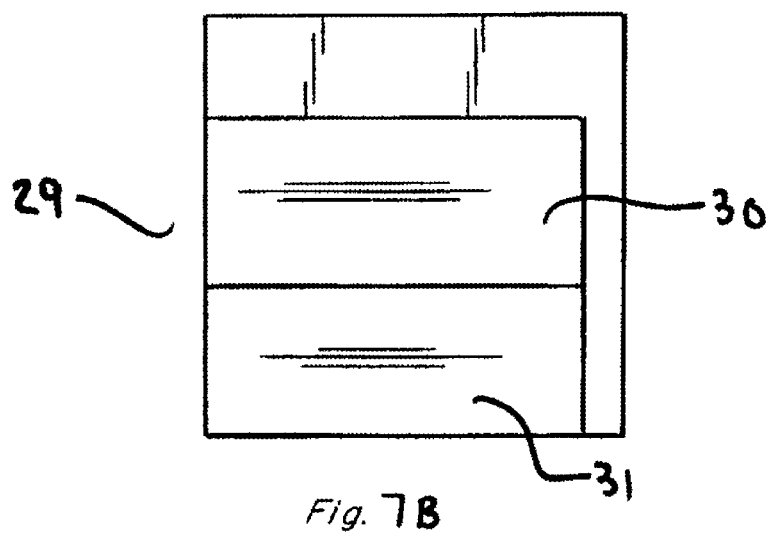
Figure 7A:
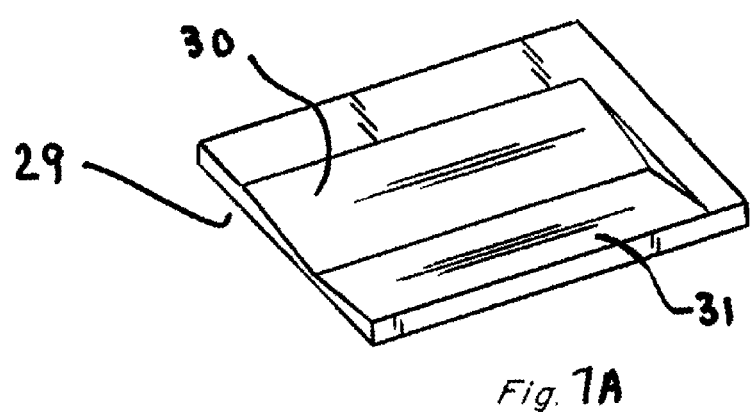
Figure 7C:
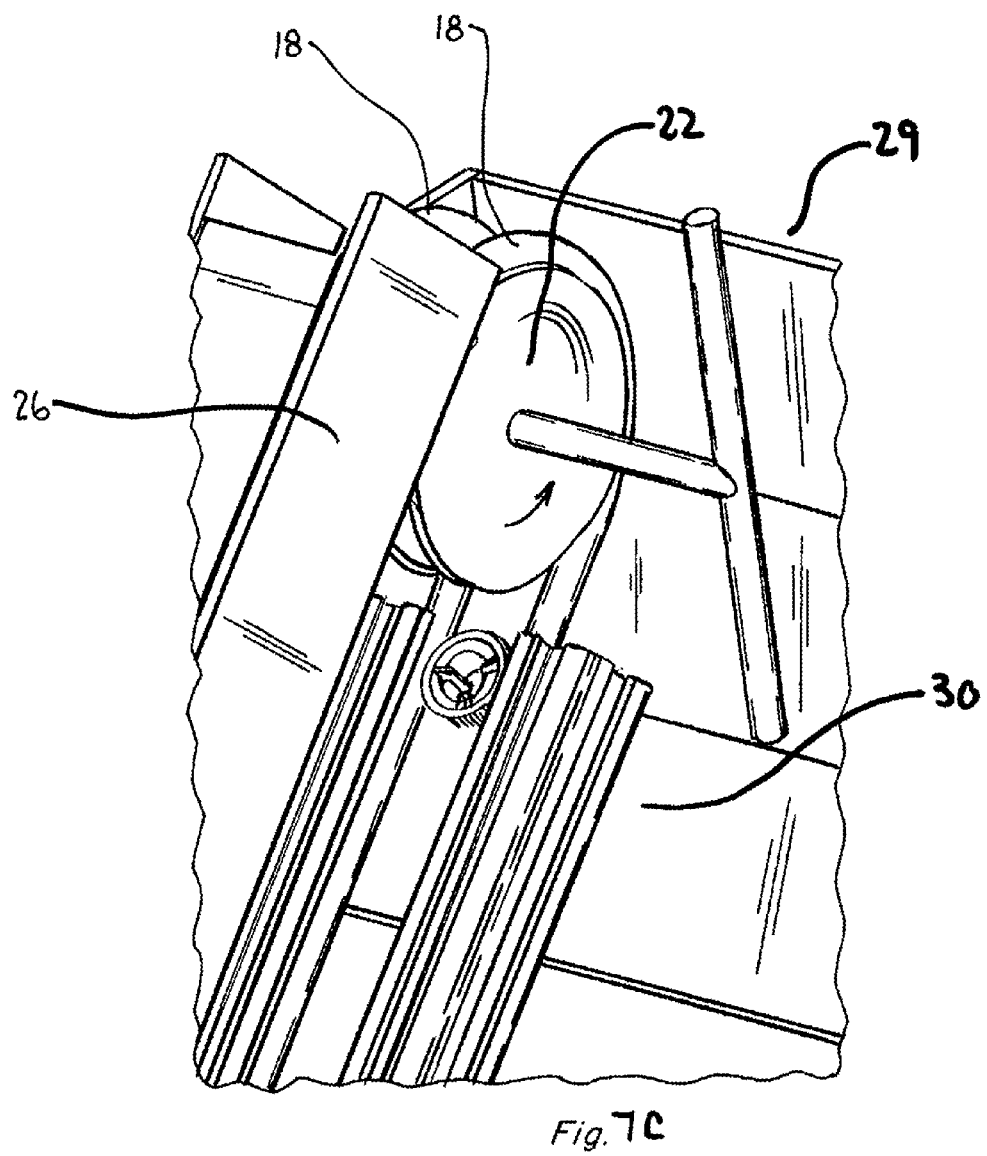
Figure 8A:
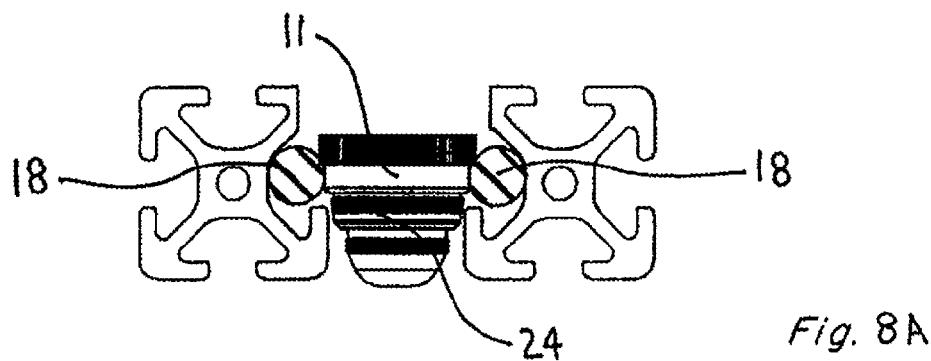
Figure 8B:
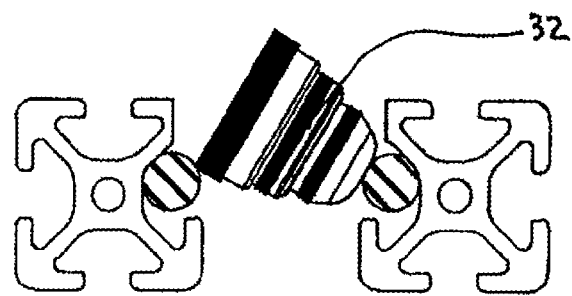
Figure 8C:
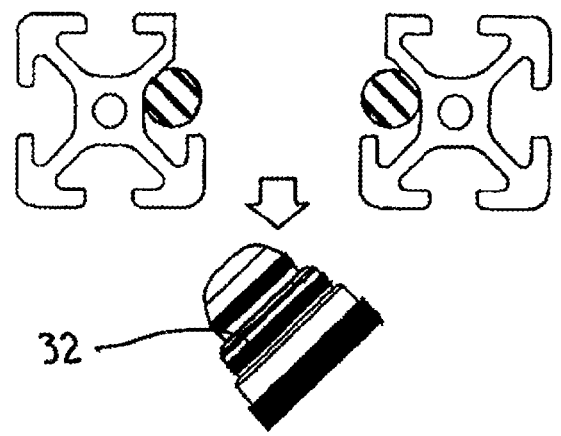
Figure 9:
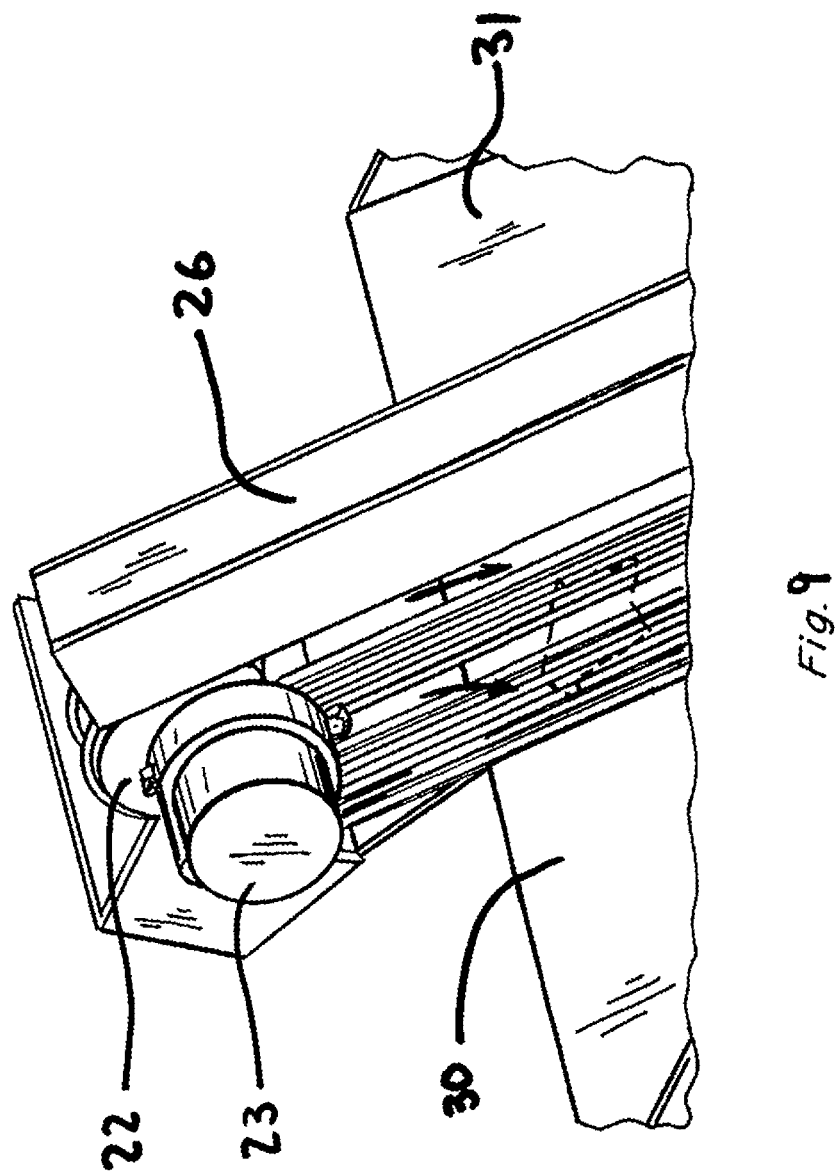
Figure 10:
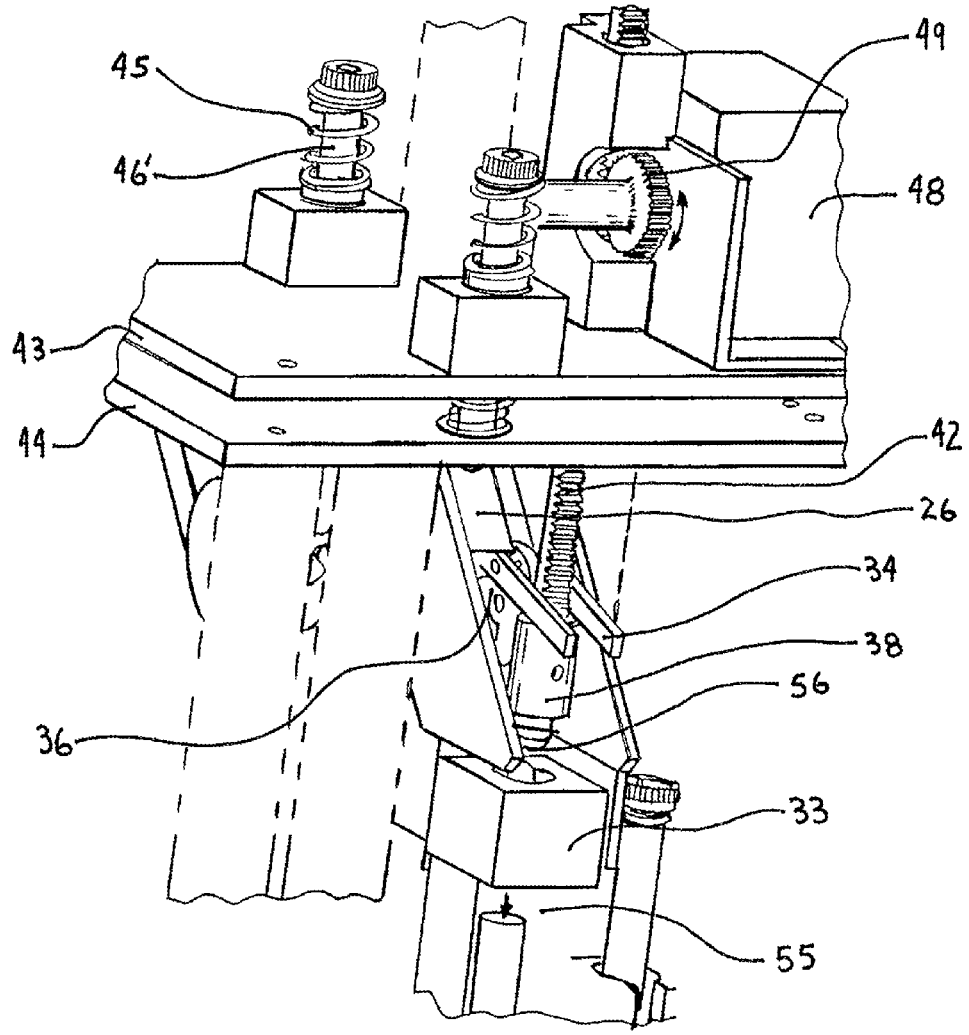
Figure 11:
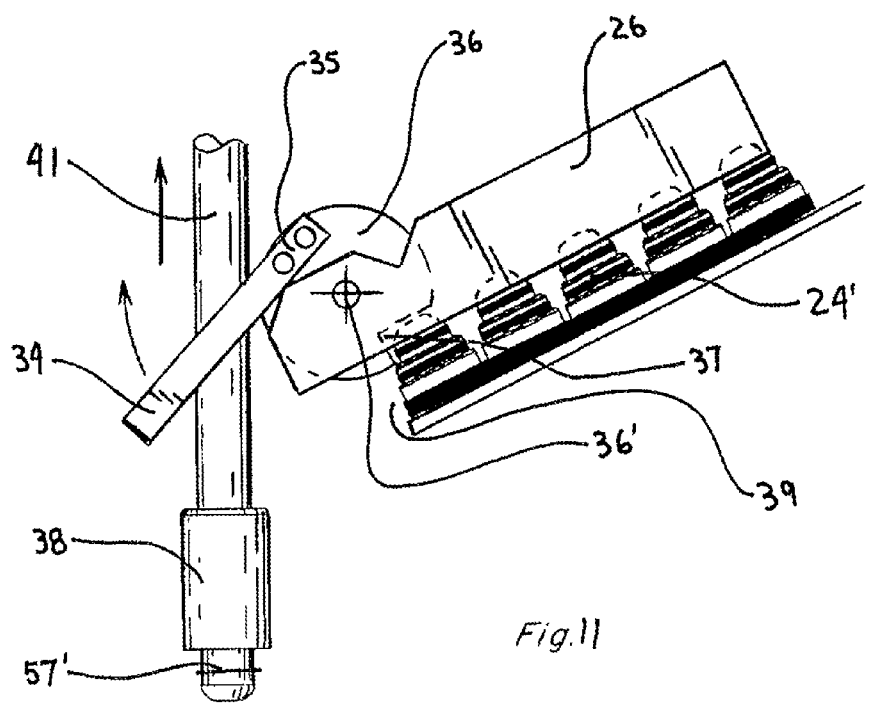
Figure 12A:
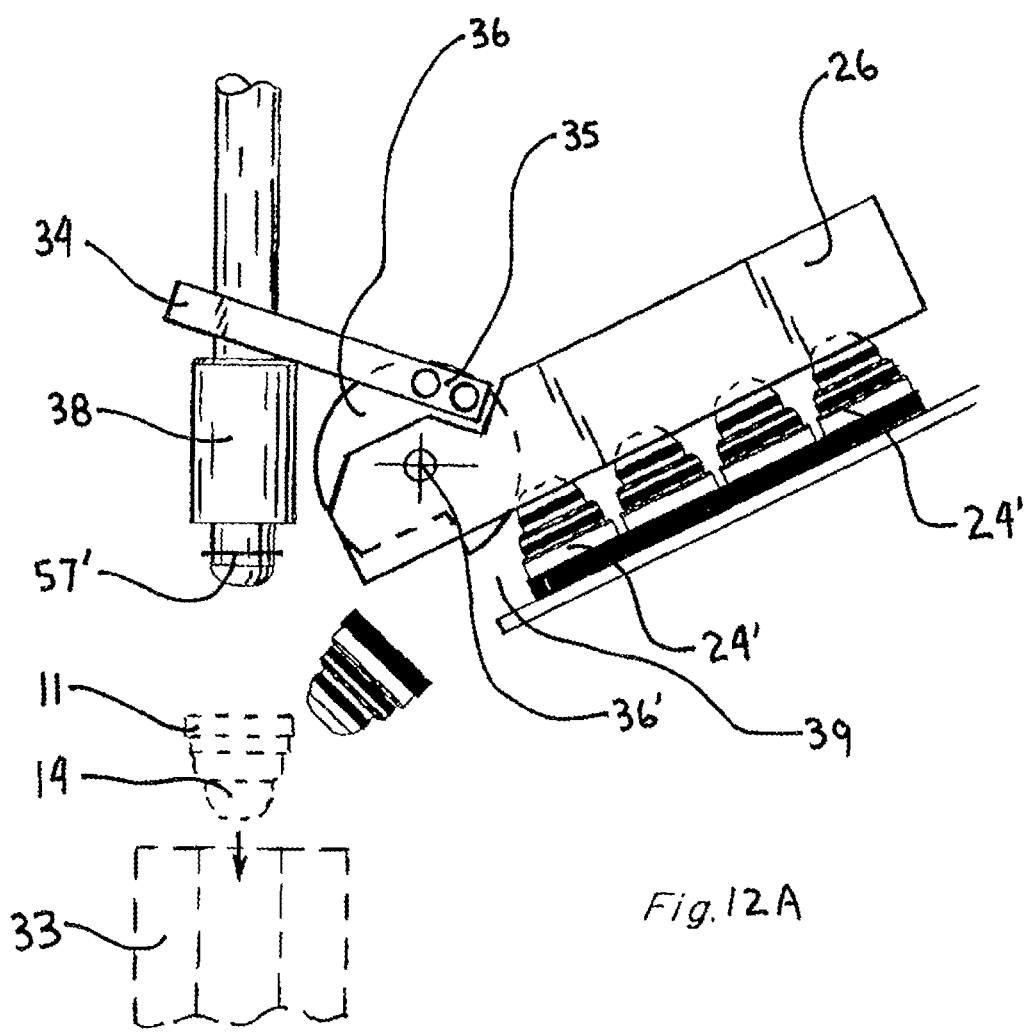
Figure 16:
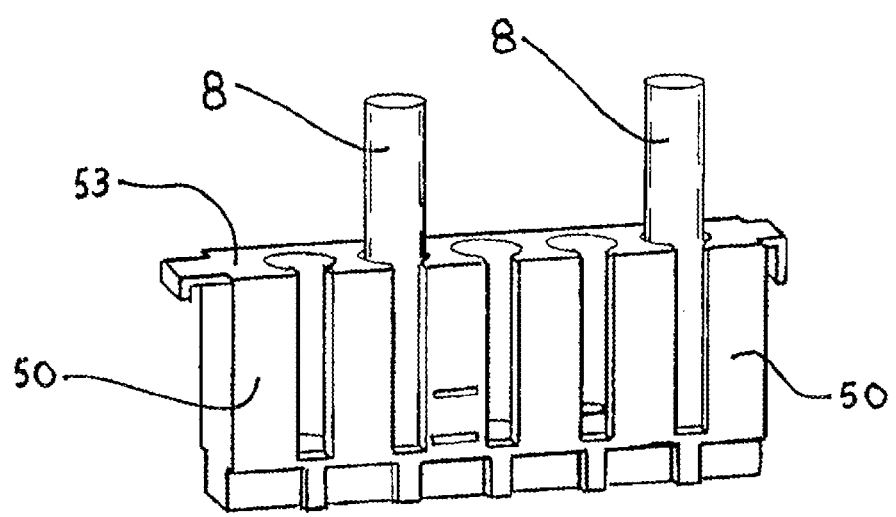
Figure 17:
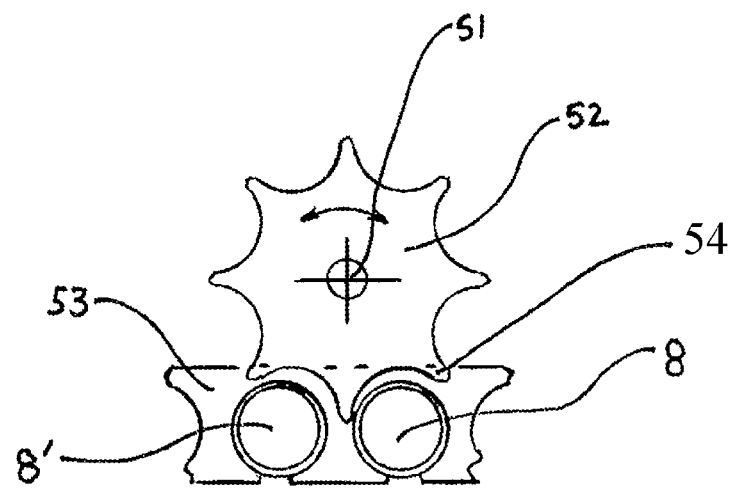
Figure 17A:
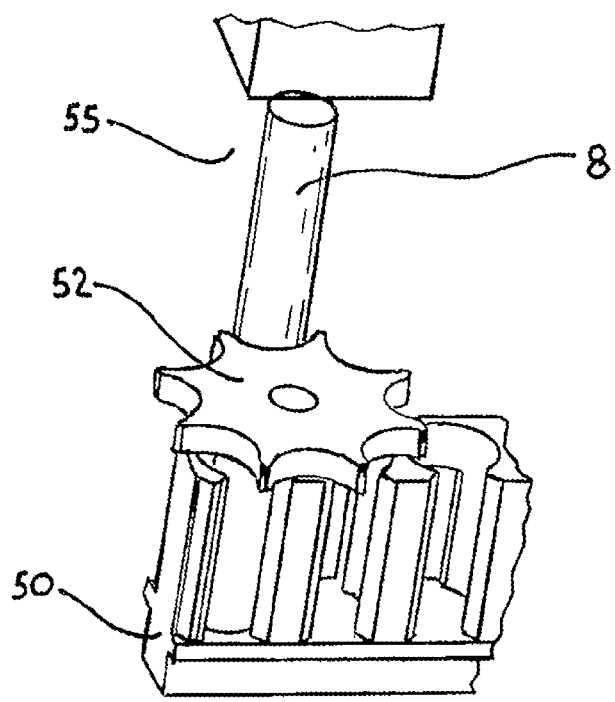
Figure 18:
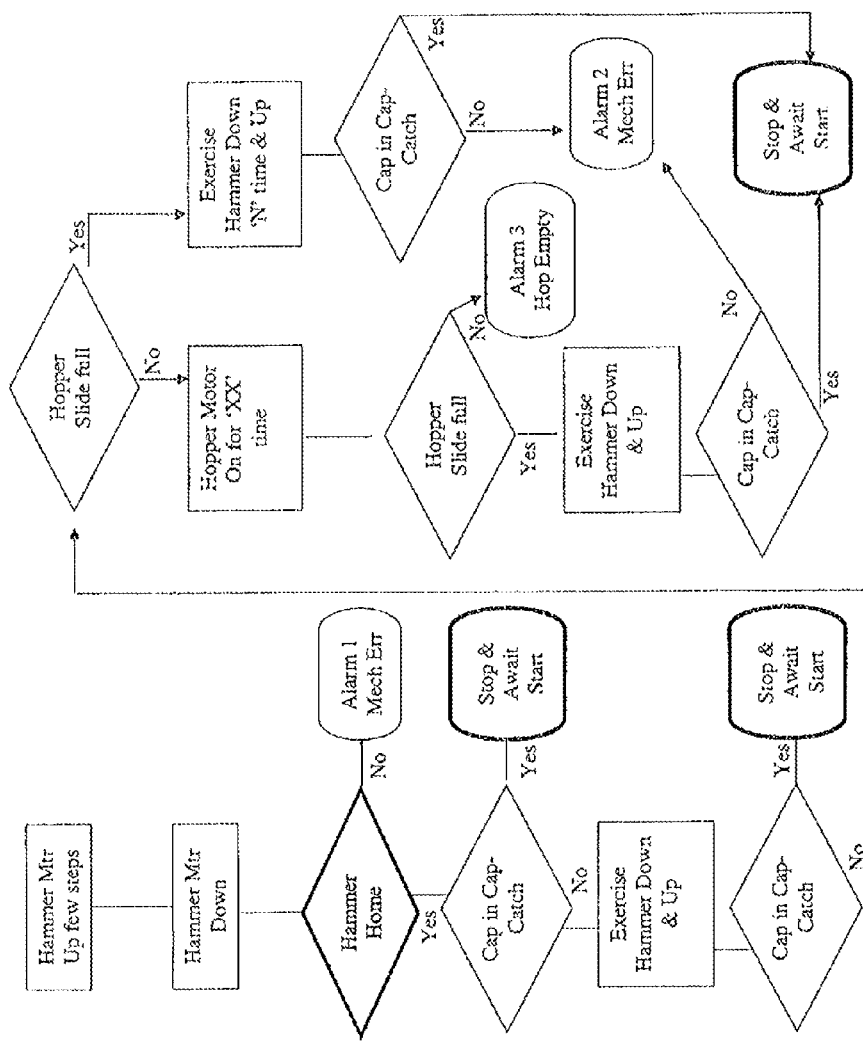
Figure 19:
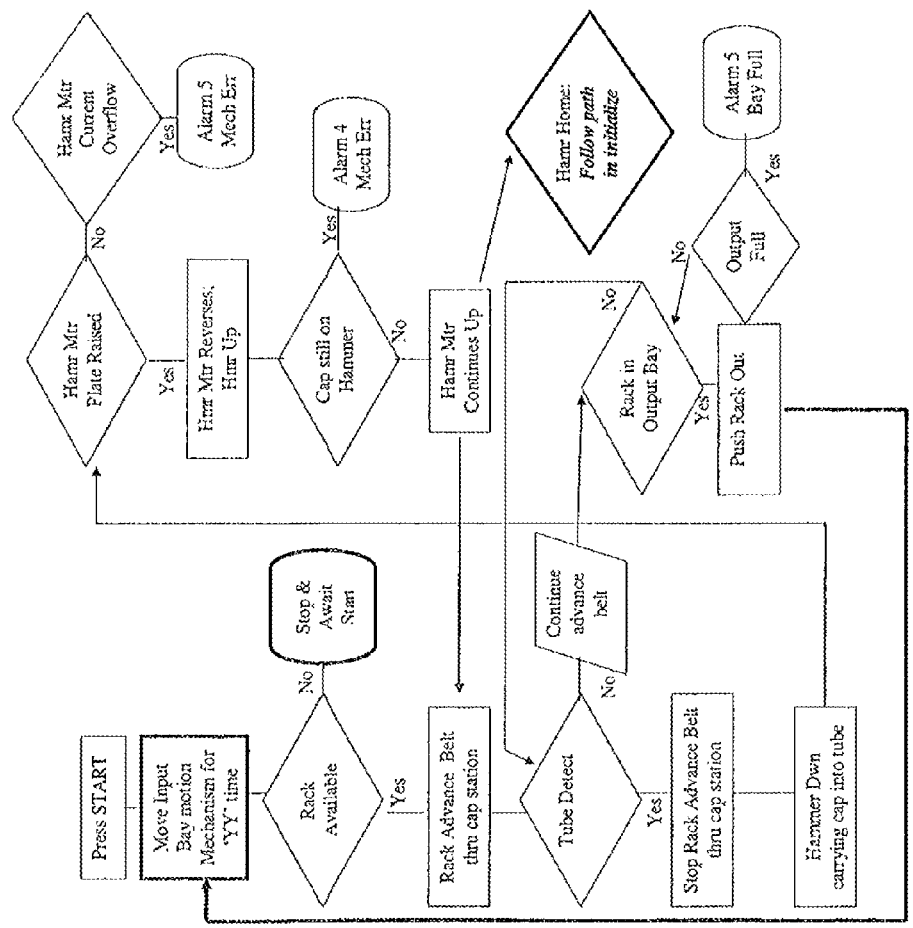

FIG. 1 is a perspective view of the device showing the major components.
FIG. 2 is a side view of the test tube cap.
FIG. 2A is a top view of the cap.
FIG. 2B is a perspective view of the top of the cap showing the notch in the nipple.
FIG. 3A is a partial top view of the hopper.
FIG. 3B is a side cutaway view of the lower part of the cap transport mechanism.
FIG. 4 is a partial perspective view of the hopper, transport and hammer assemblies.
FIG. 5 is a partial perspective view at the upper transport pulley area.
FIG. 6 is an end view of the upper transport assembly at the upper pulley.
FIG. 7A is partial perspective view of the cap reject module.
FIG. 7B is a top view of the cap reject module.
FIG. 7C is a partial perspective view of the cap reject module.
FIG. 8A is a cross-sectional view of the cap transport mechanism taken along the lines 8A of FIG. 5 showing a correctly loaded cap.
FIG. 8B is similar to FIG. 8A but shows an incorrectly loaded cap.
FIG. 8C is similar to FIG. 8B but shows the incorrectly loaded cap discharging from the belts near the top edge of the upper transport pulley.
FIG. 9 is a perspective view showing the area of the discharge of rejected caps back into the hopper.
FIG. 10 is a partial perspective view of the hammer assembly.
FIG. 11 is a partial side view of the incremental cap mechanism.
FIG. 12 is a partial top view of the incremental cap mechanism.
FIG. 12A is a side view of the incremental cap mechanism showing the cap tumbling towards the cap catch.
FIG. 13 is a partial perspective view of the lower end of the cap transport assembly and the lower end of the hammer assembly.
FIG. 14 is a perspective view of the cap catch mechanism.
FIG. 15 is a detail perspective view of the upper drive section of the hammer mechanism.
FIG. 16 is a perspective view of the test tube racks and test tubes.
FIG. 17 is a top view of the star positioning wheel.
FIG. 17A is a partial perspective view of the star positioning wheel.
FIG. 18 is a schematic diagram showing the automatic electronic functioning of the initial set up of the device.
FIG. 19 is a schematic diagram showing the automatic electronic functioning of the operation of the device.

DETAILED DESCRIPTION OF THE DEVICE

An automatic test tube recapping system 1 for placing hopper caps 3 onto test tubes comprises a cap hopper 2, a transport assembly, a cap slide 4, and a hammer assembly 6. Test tubes 8 are loaded into trays at input bay 7 and moved on a standard conveyor belt underneath the hammer assembly 6 for recapping. The random caps 3 are transported and aligned by a cap transport assembly driven by drive assembly 5, to be described later. The caps 3 slide down cap slide 4 and are positioned between the hammer shaft 41 and test tubes 8 for recapping. The area near the positioned test tubes 8, cap catch 33 and hammer shaft 41 is described as the cap position station 55. The recapped test tubes 8 and rack 50, located on lower base 10, then travel to output bay 9 to be removed from the machine and stored. These major elements of the device are shown in FIG. 1. FIG. 1 is shown as the device is commercially delivered with coverings on some components such as the transport drive assembly 5 and the hammer assembly 6. More detailed drawings of these assemblies are shown and described later in other drawings and the Specification.

The caps utilized in this machine are unique and were developed for the particular purpose of this device. The unique cap is best shown in FIGS. 2, 2A and 2B. Since most test tubes are manufactured in two diameters, either 13 or 16 mm, the cap should preferably be able to accommodate those different diameters. The standard diameters are shown by the dimension arrows on FIG. 2.

Turning to FIG. 2A, the unique shape of the instant cap is shown. The cap 3 is hollow with a conical body and has an upper circular top 11. Below the top 11 of the cap 3 is a second, middle section 12 of the cap. Section 12 is integrally connected to the top 11 and has a diameter of approximately 16 mm. Below the middle section 12 of the cap is a lower small tube section 13. This lower small tube section 13 is also integrally connected to the top 11 and middle 12 of the cap and has a diameter of approximately 13 mm. The top, middle and lower sections all have flanges adapted to receive various diameter test tubes. The bottom of the cap 3 has a rounded end 14. Most other test tube caps do not have the two distinct sections 12 and 13 or the rounded end 14. The rounded end 14 helps to insert the cap 3 into a test tube 8 even if the central axis of the cap and test tube are slightly off center.

The inside surface of cap 3 has an added feature unique to this invention. The inner surface has a plurality of nipples 15, spaced apart from each other, as best shown in FIG. 2A, for receiving and gripping the hammer shaft. At least one but preferably three equally spaced nipples 15 are shown in the drawing figure and are preferred, but a different number of nipples or spacing of the nipples is still within the spirit and disclosure of this invention. Each nipple 15 has a notch 57 removed therefrom. This notch 15 is adapted to receive a small circumferential raised ridge 57' located on the very lower end of hammer shaft 41. The nipples 15 and notch 57 allow the caps to remain on the lower end of the hammer drive shaft 41 and to be removed therefrom during operation of the invention.

Turning now to FIG. 3A, the construction and configuration of the hopper 2 is shown. The hopper has an essentially square cross-section from the top and an essentially triangular cross-section from top to bottom. The inside sides 16 of the hopper 2 are essentially triangular and slant inwardly from top to bottom as shown. Running through the approximate center of the hopper at its lowest central point 17 is a transport beltway 19.

The beltway is best shown on FIGS. 3A, 3B, 4 and 6. The beltway housing comprises identical, mirror image sides 19' as best shown on FIG. 6. Each side 19' of the beltway has an indented metal surface designed to accept a pair of left and right identical and continuous silicon transport belts 18. The beltway runs from the lower, bottom 17 of the hopper 2, through one side of the hopper, and upwards toward the upper cap transport drive assembly 5.

At the lower end of the transport assembly are two pulleys 20 and 21. The hopper pulleys 20 and 21 are located near the surface of hopper side 16 as shown in FIGS. 3A and 3B. The discharge drive pulley 21 is located above the hopper 2 and near the top of the cap slide 26.

Belts 18 are continuous and wrap around lower pulleys 20 and 21 and upper transport drive pulley 22. The drive pulley 21 turns in the counterclockwise direction in FIG. 3B, driving the belts 18 in the direction of the arrow, from left to right on the lower part of the transport mechanism and right to left on the upper part of FIG. 3B.

FIG. 4 shows the position of the various assemblies in relation to each other in the device. The lower part 19" of the belt way is the part that runs through the inner hopper surface. This lower beltway 19" carries caps upwards to the top part of the device, near the pulley drive motor 23. Randomly deposited hopper caps 3 fall into the beltway and onto the silicon belts 18 and are transported on the belts to the top of the device. Properly positioned caps are then reversed, as will be explained, and travel down cap slide 26 to the recapping position. Turning now to FIGS. 5 and 6, the operation of the beltway and belts is shown. The device has a belt drive means comprising an upper drive pulley 22 connected to drive motor 23 and drive motor output shaft 23' as shown and at least one lower pulley. The drive motor 23 moves the belts 18. Belts 18 are preferably made of urethane but can be made of other materials as well. Caps drop onto the beltway in a random orientation. Many caps will fall into proper alignment. A properly aligned cap 24 is held between the pair of belts 18 by frictional forces. FIG. 5 shows the properly aligned cap 24 as it approaches the very top of the transport assembly.

As the properly aligned cap 24 is positioned on the upper pulley 22, near the upper part of the cap slide 26, its orientation is reversed 24', as best shown in FIG. 6. The upper drive pulley 22 has a central circumferential discharge ridge 25 located in the center of the upper drive pulley 22 as shown. This discharge ridge is important to the discharge and recycling of improperly aligned caps, as will be explained later.

The cap slide 26 runs above the lower part of the continuous transport beltway as shown in FIG. 6. At the top of the cap slide 26 is a cap slide groove 27. The smaller, rounded end 14 of a properly aligned reversed cap 24' rides in the cap slide groove 27. The gripping top 11 of the reversed cap 24' rides on a cap slide guide 28. The properly aligned cap 24' slides down cap slide 26 into the lower, loading position, as will be explained later. As can be seen from the drawing figure, the belts 18 are completely disengaged from contact with the reversed cap 24' at this point.

Located at the upper end of the continuous beltway near the drive motor 23 and drive pulley 22 is a cap reject module 29, as best shown in FIGS. 7A, 7B and 7C. (The top view of FIG. 7B is rotated 90 degrees clockwise from FIG. 7C.) This cap reject module has an irregular shape, as best shown in FIGS. 7A and 7B. The reject module has a slanted surface 30 located under the belts 18 that is slanted downwardly and away from the drive pulley 22. This slanted surface 30 is integrally connected to a cap discharge surface 31. The cap discharge surface 31 is slanted downwardly toward the hopper bin, as shown in FIG. 9. Improperly aligned caps will fall to the bottom right of FIG. 9 and are recycled into the hopper bin 2. The upper part of the device and hopper bin 2 are best shown in FIG. 1.

Since the hopper caps 3 fall onto the transport belts in a random fashion and orientation, some caps will not lodge between the belts with the top suspended by the belts and the bottom oriented downward as is the case of a properly aligned cap 24 shown on FIG. 8A. An improperly suspended cap 32, as best shown of FIG. 8B, would lay in the general horizontal orientation or in some other oblique orientation as shown. Since the diameter of a cap gripping top 11 is shorter than the length of the cap from top to bottom, a cap that does not fall as shown in FIG. 8A will fall onto and ride upon the belts 18 in an improper orientation a shown in FIG. 8B.

As the improperly oriented cap 32 rides upwards and reaches the area of the upper part of the cap slide 26 and upper transport pulley 22, the improperly aligned cap 32 either falls off the transport belts 18 by the force of gravity or comes into contact with pulley discharge ridge 25 which forces the improperly orientated cap 32 off the belts 18 supporting it as shown in FIG. 8C. Either way, the rejected improperly aligned caps 32 fall onto surface 30. Improperly aligned caps 32 fall onto the top slanted surface 30 of the reject module 29, and roll by gravity toward surface 31 and ultimately back into the hopper.

Whereas a properly aligned cap 24, aligned as shown in FIGS. 8A and 6, will stay suspended by the belts 18, an improperly aligned cap 32 will fall from the belts 18 to be recirculated into hopper 2.

As best shown in FIGS. 5 and 6, the path of the properly aligned and reversed cap 24' is shown. A cap slide 26 has a top end located on the top of said hopper and slopes downwardly towards a lower cap catch. The cap slide 26 houses the smaller part 13 of the cap and the cap top 11 slides on the cap slide guide 28. Reversed cap 24' slides down the cap slide 26 to the bottom of the slide. The cap slide slopes downwardly toward the lower cap stop station.

As best shown on FIG. 10, located at the end of the slide 26 is a cap catch 33. Hammer shaft 41 is above the bottom of cap slide 26 and cap catch 33 as shown. Upside down but correctly loaded reversed caps 24' are incrementally allowed to tumble into cap catch 33 by the mechanism best shown on FIGS. 11 and 12.

A pair of cap incremental loading arms each has a lower end 34 and an upper end 35. The upper ends 35 of the loading arms are rotatably connected to a cap incrementing disc or wheel 36. The upper ends 35 of the loading arms are connected in an off-center position on disc 36 as shown to create a circular motion of the disc when the arms are pushed upwards. The incrementing wheel 36 rotates about its central axis 36'. Disc 36 has a cap receiving cut-out 37, shown on FIG. 11 in phantom lines, removed from it as shown. The cut-out makes the disc resemble a PAC-man icon. This cut-out 37 is adapted to receive one cap 24' for each cycle of the loading arms.

The lower part 34 of the loading arms is slidably connected to the hammer shaft 41 above the cap incrementing lift 38. The incrementing lift 38 is permanently attached to the hammer shaft 41. As the hammer shaft 41 cycles, it rises and lifts the cap incrementing lift 38, which in turn lifts the loading arm, which rotates the cap incrementing disc 36. The disc then cycles a new single cap 24' per cycle into the cap catch 33.

As each single cap 24' is allowed to slide down the cap slide 26 past the incrementing disc 36 to the very bottom 39 of the cap slide, cap 24' tumbles into cap catch. The force of gravity and the orientation of the slide causes the cap 24' to flip over 135 degrees such that the top 11 of the cap is now orientated towards the top of the device and the bottom 14 of the cap is orientated downward.

The cap catch 33 may be funnel-shaped or square shaped but has three flat edges, parallel edges 33' and third edge 33". The three flat edges of the cap catch are connected by cap catch spring 40. The cap top 11 has a flange as shown in FIG. 2A. The top flange is slightly smaller than the length between parallel edges 31' of the cap catch such that the cap 24 tumbles into the cap catch 33 as shown in FIG. 14. The spring 40 retains the cap 24' in the cap catch 33 until the hammer shaft 41 drives the cap 24' downwards.

Located above cap catch 33 is a hammer shaft 41. Hammer shaft 41 is located directly above cap catch 33 as shown in FIG. 13. Hammer shaft 41 is a long cylindrical shaft with teeth 42 located on the shaft. Shaft 41 also has incrementing lift 38 attached to it near the bottom of the shaft. The loading arms are slidably connected on each side of the hammer shaft. The lower end 34 of left and right loading arms are positioned on each side of the shaft and above the lift 38. Each time the hammer shaft 41 is raised, it pushes the ends 34 of the loading arms, which rotates the incrementing disc 36 such that another single cap 24 is ready to slide down the cap slide 26 and tumble into the now empty cap catch 33.

Turning now to FIGS. 10, 14 and 15, the hammer plunger assembly is described. Above cap catch 33 and bottom of cap slide 39 are two platforms. Hammer assembly upper plate 43 is located above hammer assembly lower plate 44 (FIG. 10). Lower plate 44 is supported by lower plate leg supports 47 legs and connected to the base 10 of the device as shown on FIG. 1. The upper plate 43 is movably connected to lower plate 44 by lower springs 46. Rods 46' connect the plates 43 and 44 as shown. Positioned around the upper part of connecting rods 46' are upper springs 45. Upper plate 43 is virtually suspended by springs 46 but the upward movement of upper plate 43 is limited by upper springs 45.

A reversible drive motor 48 is fixedly attached to the top of plate 43 as shown. This drive motor has a drive gear 49 that mates with the teeth 42 on hammer shaft 41. As the drive motor turns counterclockwise as shown in FIG. 15, the hammer shaft 41 moves on its downward stroke. When the lower end 56 (FIG. 10) of hammer shaft 41 contacts the properly positioned cap 24' positioned in cap catch 33, the end of the hammer shaft moves into the inside of the cap and pushes on cap nipples 15. As the hammer moves further downwardly, the spring 40 of cap catch 33 is forced outwardly, the edges 33' of cap catch 33 expand and the cap 24' is pushed out of the cap catch. This action is shown best on FIG. 13. Due to the frictional pressure between the lower end of the hammer shaft 41 and the nipples 15, the cap 24 remains stuck to the end of shaft 41 as best shown in FIG. 13.

Cap 24' is now frictionally loaded onto the end of hammer shaft 41. One of the sections, 12 or 13, of the cap is then firmly driven into the top of test tube 8. If the test tube has a 13 mm diameter, the flange of section 13 seals the test tube; if the test tube has a 16 mm diameter, the flange of section 12 seals the test tube.

As the flange of the cap contacts the top rim of test tube 8, the cap is in place and firmly secured. The hammer 41 now bottoms out. However, because plate 43 is spring loaded, top plate 43 along with the hammer motor 48 rise upwardly. The upward motion of the top plate 43 is detected electronically and causes the motor to reverse direction, withdrawing the hammer shaft 41 from the cap 24'. The stationary, spring loaded lower plate 44 absorbs the top plate falling down as shaft 41 releases the force lifting the top plate when it reversed its motion.

The binding force between the cap fully inserted into the test tube and firmly seated is greater than the snap force between the nipples 15 and the bottom of the hammer shaft. Therefore, when the hammer shaft moves upwards, the hammer shaft is released from the seated cap.

The upward motion of the shaft 41 creates contact between the upper part of lift 38 and the lower ends 34 of loading arms, which recycles the loading arms and allows a single new cap 24' to be loaded into cap catch 33.

One cap per cycle is loaded into the cap stop station. As the test tube is recapped, the hammer shaft withdraws upwardly, moving the loading arms and allowing another single cap to tumble onto the cap catch. The conveyor then automatically moves the test tube rack one test tube and positions another uncapped test tube under the cap and hammer shaft per cycle.

Test tubes 8 are loaded onto test tube racks 50 in a single line as shown in FIGS. 16 and 17. The test tubes 8 may be of varying diameters due to the unique sections 12 and 13 of the caps 3. Further, because the hammer shaft may travel various distances before capping a test tube and bottoming out, the test tubes may also be of varying heights.

A positioning star 52 rotates around a hub 51 to incrementally detect the next test tubes as the assembly line proceeds. The next test tube is automatically advanced by the electronics. Horizontal positioning star 52 is located above the rack top 53 and between test tubes 8 and allows only one uncapped test tube at a time to be positioned at the cap catch station 55 located under the hammer shaft 41 and cap catch 33. As a test tube is capped, the rack conveyor pushes the racks toward the outlet bay. Tine 54 is pushed from left to right in FIG. 17, releasing test tube 8, now capped in its rack, to move towards the outlet bay. The next test tube in line, 8' is then moved left to right and positioned at the cap stop station, under the cap catch 33 and hammer shaft 41 for the next capping cycle.

The device has many safety features and alarms so that automatic operation is accomplished. The electronic operation of the device, including the function of the sensors and meters, is best shown diagrammatically in FIGS. 18 and 19.

As shown in Diagram 18, the device has sensors to detect whether or not the recapping cycle may begin. The first action is to move the hammer shaft 41 up a few steps. The reversible motor 48 then reverses and moves the hammer shaft downwards to a "Home" position, ready to recap the test tube provided a cap is in the cap catch. If the hammer does not reach the "Home" position, Alarm 1 is activated signaling a "Mechanical Error." If the hammer is correctly positioned in the "Home" position, the device electronically checks to determine if a cap 3 is in the cap catch 33. If the hammer shaft 41 is in the "Home" position and a cap is in the cap catch, the device is programmed to stop and await the "Start" command.

If a cap 3 is not in the cap catch 33, the device cycles the hammer up and down again, which will cycle the loading arms 34-35 which should allow another cap to load into the cap catch. The device again checks for the presence of a cap in the cap catch. If a cap is now loaded into the cap catch, the device will stop and wait for the "Start" command.

If a cap is not now loaded in the cap catch, the device will then electronically check the cap slide 26 (referred to as "hopper slide" in FIG. 18) and hopper 2. First, sensors detect if the cap slide 26 is full. If it is, the device cycles the hammer shaft up and down through one or more cycles ('N') to again cycle the loading arms to advance the incremental disc 36. If a cap is now in the cap catch, the device will stop and wait for the "Start" command. If not, the device signals another "Mechanical Error" in the cap advance system and Alarm 2 will be activated.

If the cap slide 26 is not full on initial detection, the device automatically turns on the transport drive motor 23 (referred to as "hopper motor" in Diagram 18) for a period of time ('XX'). This operation should load more caps into the cap slide if caps are available. If this operation does not result in the cap slide sensor showing a full cap slide, Alarm 3 will be activated showing that the hopper 2 is empty. However, if the cap slide 26 is now full, the hammer shaft cycles, which should load a cap 3 in cap catch 33. If the device now senses a cap in the cap catch, it will stop and wait for the "Start" command. If a cap is still not in the cap catch Alarm 2 will be activated.

Sensors that are capable of determining if caps or other moving pieces of the invention are located in a particular position are well known in the art. These sensors, in and of themselves, alone and apart from the other mechanism shown and described herein, are not considered to be part of the novelty of this device.

Once the device determines that a cap 3 is in the cap catch 33 and the hammer shaft 41 is in the "Home" position, the device is ready to start. The operation of the device from the "Start" position will now be described.

Turning now to FIG. 19, a "Start" switch starts the input bay conveyor in motion for "YY" seconds, set by the operator, once the initializing procedure (FIG. 18) is set for "Start." If a rack 50 of test tubes 8 is available, the rack 50 advances on the conveyor through the cap station 55. A single test tube 8 passes through the positioning star 52 until an uncapped test tube 8 is positioned under the cap catch 33. The rack conveyor then stops. The uncapped test tube 8 need not be exactly centered under the cap 24' since the cap 24' has a rounded lower end 14. The rounded lower end allows the cap 24' in cap catch 33 to be pushed into the uncapped test tube 8 even if it is slightly off-center. Once the test tube is positioned, the hammer shaft drives the cap into the test tube and recaps the test tube. The hammer shaft bottoms out on the top edge of the test tube and the hammer base upper plate 43 is raised. The hammer motor 48 then reverses, the cap is released from the lower end of the hammer shaft, and the hammer shaft continues upwards until it reaches its "Home" position. As this action is cycled another uncapped test tube is advanced under the cap catch. The next cycle then begins with a new cap and uncapped test tube positioned in the correct recapping position.

Several safety features are built into the operation system of the invention. If for some reason the hammer shaft continues to drive the cap 24' downward into the test tube without raising the hammer base plate 43, a current overflow meter on the hammer motor 48 will stop the motor movement and activate Alarm 5. If the cap 24' is not released from the bottom of the hammer shaft 41, Alarm 4 will activate. Alarms 4 and 5 signal to the operator that a mechanical error has occurred.

If no uncapped test tube is detected after the conveyor continues to advance the rack, all of the test tubes from that rack are now recapped. The fully recapped test tube rack is then conveyed into the output bay and the finished rack of recapped test tubes is pushed out of the device. Once this is accomplished, the device automatically advances the next rack of uncapped test tubes from the input bay to the tube detection station under the cap catch and the cycle repeats itself for each uncapped test tube in the next rack. If the output bay is full, Alarm 5 will activate to signal to the operator that the output bay is full. The output bay must then be emptied before another rack from the input bay is conveyed to the cap catch station.

Sensors that are capable of determining if an uncapped test tube, a recapped rack of test tubes or other moving pieces of the invention are located in a particular position are well known in the art. The current overflow meter of the hammer motor is also well known in the art. These sensors and meters, in and of themselves, alone and apart from the other mechanism shown and described herein, are not considered to be part of the novelty of this device.

This device is operated by a PLC, a programmable logic circuit. The PLC is the "brain" of the device and directs the various motors, sensors and meters to perform the functions described above. The function and operation of a PLC is well known in the art. The programming of the PLC to perform the above functions is not, in and of itself, apart from the device mechanisms described, considered to be part of the novelty of this invention. A person with ordinary skill in the art can program the PLC to perform the functions described herein.

Obviously, it is the interaction of the various major elements of this invention that comprise the novelty of the device. Minor variations of the parts and substitution of certain of the elements with equivalent elements is within the disclosure and novelty of this device. For example, the hopper 2 could take a slightly different shape or the beltway could be placed slightly differently. However, the disclosure herein is considered to be of the preferred embodiment.

The invention claimed is:

1. An automatic recapping device for recapping test tubes with caps, comprising:
    (a) an upper hopper having an essentially triangular cross-section for receiving test tube caps;
    (b) a pair of continuous transport belts separated by the diameter of the top of the circular cap in said hopper for transporting said caps to the top of an upper slide, further comprising a belt drive means for said belts and upper and lower transport pulleys for moving said transport belts in a continuous manner;
    (c) a cap slide having a top end on the top of said hopper sloping downwardly towards a lower cap catch;
    (d) a cap catch near the bottom of said cap slide adapted to receive one cap per cycle, said cap catch located above an uncapped test tube and below a hammer shaft;
    (e) a hammer shaft mechanism located above said cap catch, having a hammer shaft driven by a reversible motor wherein said shaft and motor are attached to a hammer motor base;
    (f) a test tube conveyor system that moves one uncapped test tube per cycle under said cap catch;
    (g) further comprising an incremental discreet cap loader having a loading arm, wherein the lower part of said arm is slidably attached to said hammer shaft and the upper part of said cap loader having a disc with a cutout for discreetly loading a single cap per cycle;
    wherein, in each cycle of said device, a test tube cap is automatically loaded from said hopper into said cap catch and driven into an uncapped test tube.

2. A test tube recapping device as in claim 1, further comprising a positioning star located at the bottom of said cap catch between individual test tubes for positioning one uncapped test tube per cycle for recapping.

3. A test tube recapping device as in claim 1, further comprising position sensors for detecting the location of the hammer shaft.

4. A test tube recapping device as in claim 1, further comprising position sensors for detecting the presence of a cap in said cap catch.

5. A test tube recapping device as in claim 1, further comprising position sensors for detecting the presence of caps in the cap slide.

6. An automatic recapping device for recapping test tubes with caps, comprising:
    (a) an upper hopper having an essentially triangular cross-section for receiving test tube caps;
    (b) a pair of continuous transport belts separated by the diameter of the top of the circular cap in said hopper for transporting said caps to the top of an upper slide, further comprising a belt drive means for said belts having upper and lower transport pulleys for moving said transport belts in a continuous manner;
    (c) a cap slide having a top end on the top of said hopper sloping downwardly towards a lower cap catch;
    (d) a cap catch near the bottom of said cap slide adapted to receive one cap per cycle, said cap catch located above an uncapped test tube and below a hammer shaft;
    (e) a hammer shaft mechanism located above said cap catch, having a hammer shaft driven by a reversible motor wherein said shaft and motor are attached to a hammer motor base wherein said hammer motor base is spring loaded, wherein when said hammer bottoms out when recapping a test tube, said hammer motor base rises and said hammer motor reverses;
    (f) a test tube conveyor system that moves one uncapped test tube per cycle under said cap catch;
    wherein, in each cycle of said device, a test tube cap is automatically loaded from said hopper into said cap catch and driven into an uncapped test tube.

7. A test tube recapping device as in claim 6, said hammer base further comprising a position sensor for reversing the direction of said hammer motor when said hammer base rises.

8. An automatic recapping device for recapping test tubes with caps, comprising:
    (a) an upper hopper having an essentially triangular cross-section for receiving randomly oriented test tube caps each cap having an upper circular cap diameter;
    (b) a pair of continuous transport belts separated by the diameter of the top of the circular cap running from the lower bottom of said hopper, through one side of the hopper, and upwards toward the upper cap transport drive assembly for transporting said caps to the top of an upper slide, wherein caps drop onto said pair of transport belts in either a properly aligned or improperly aligned orientation further comprising a belt drive means for said belts having upper and lower transport pulleys for moving said transport belts in a continuous manner, said belt drive means further comprising at least one lower pulley and at least one upper discharge pulley connected to a drive motor, wherein said upper discharge pulley has a central circumferential ridge to eject misaligned caps;
    (c) a cap slide having a top end on the top of said hopper sloping downwardly towards a lower cap catch;
    (d) a cap catch near the bottom of said cap slide adapted to receive one cap per cycle, said cap catch located above an uncapped test tube and below a hammer shaft;
    (e) a hammer shaft mechanism located above said cap catch, having a hammer shaft driven by a reversible motor wherein said shaft and motor are attached to a hammer motor base;
    (f) a test tube conveyor system that moves one uncapped test tube per cycle under said cap catch;
    wherein, in each cycle of said device, a test tube cap is automatically loaded from said hopper into said cap catch and driven into an uncapped test tube.

* * * * *